United States Patent [19]
Kushner et al.

[11] Patent Number: 6,156,723
[45] Date of Patent: Dec. 5, 2000

[54] COMPOSITIONS COMPRISING INHIBITORS OF ESTROGEN RESPONSE

[75] Inventors: Peter Kushner; Paul Webb; Renee Williard; C. Anthony Hunt; Gabriella Lopez, all of San Francisco, Calif.

[73] Assignee: The Regents of the University of California, Oakland, Calif.

[21] Appl. No.: 08/930,455

[22] PCT Filed: Mar. 26, 1996

[86] PCT No.: PCT/US96/04104

§ 371 Date: Jan. 12, 1998

§ 102(e) Date: Jan. 12, 1998

[87] PCT Pub. No.: WO96/30505

PCT Pub. Date: Oct. 3, 1996

Related U.S. Application Data

[63] Continuation-in-part of application No. 08/410,807, Mar. 27, 1995, Pat. No. 5,723,291, which is a continuation-in-part of application No. 08/115,161, Sep. 1, 1993, abandoned.

[51] Int. Cl.[7] .......................... A61K 31/00; A61K 31/55; A61K 31/35

[52] U.S. Cl. .................. 514/1; 514/45; 514/211; 514/280; 514/455; 514/456; 514/651

[58] Field of Search ................... 514/12, 2, 211, 514/280, 45, 651, 455, 456, 1

[56] References Cited

FOREIGN PATENT DOCUMENTS

WO 95/06754  3/1995  WIPO .

*Primary Examiner*—Elizabeth Kemmerer
*Attorney, Agent, or Firm*—Skjerven Morrill MacPherson LLP; Tom Hunter

[57] ABSTRACT

The present invention provides novel assay methods for identifying compounds that may have both estrogen agonist and antagonist properties. In particular, the assay use cells comprising promoters having an AP1 site linked to a reporter gene. Compounds capable of inducing or blocking expression of the reporter gene can thus be identified. The compounds may be further tested for the ability to modulate the standard estrogen response, as well.

6 Claims, 10 Drawing Sheets

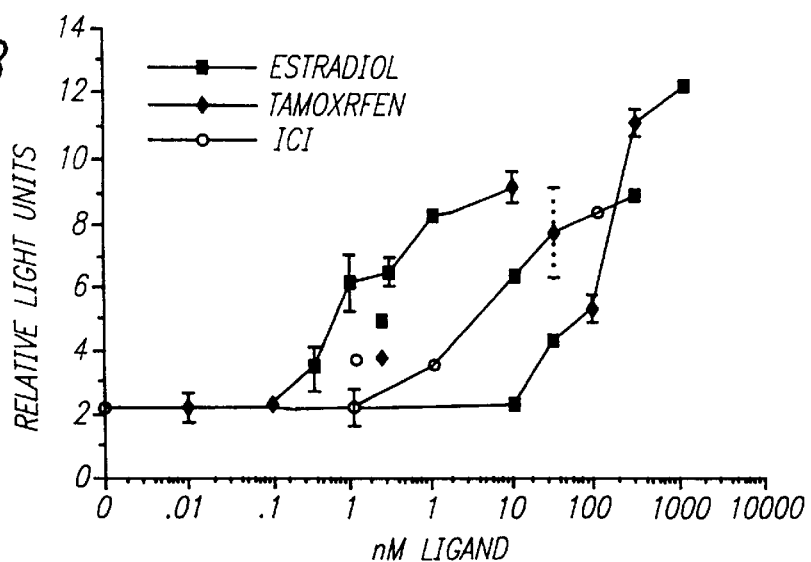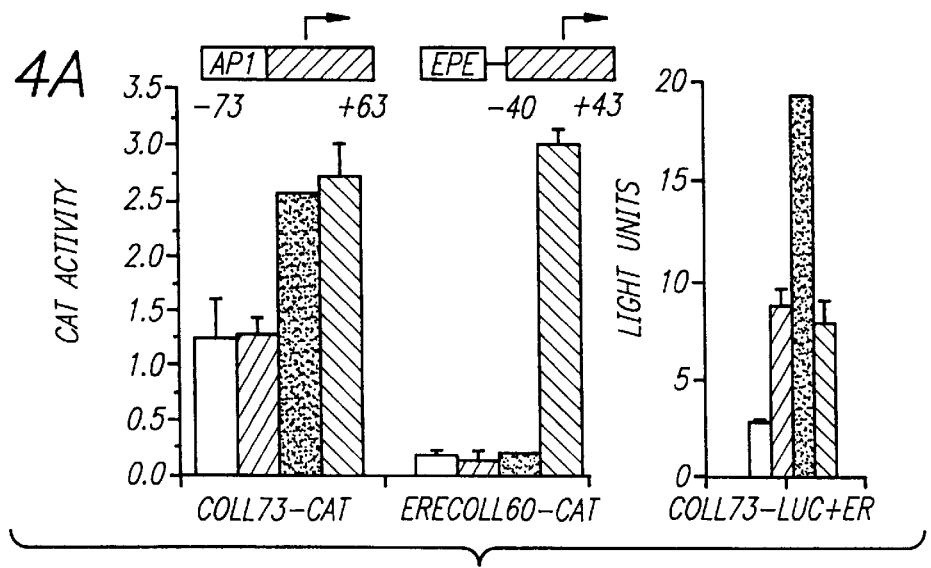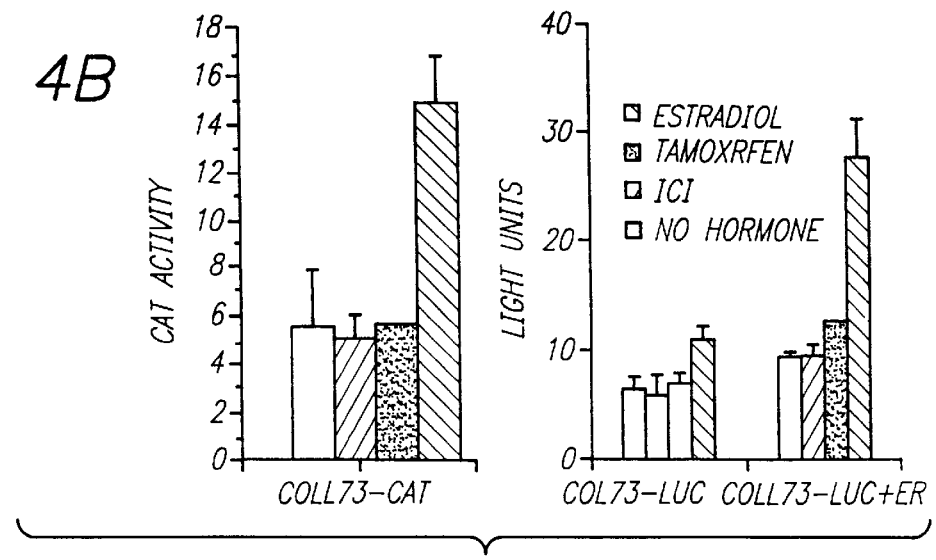

| COMPOUND | R1 | R2 | R3 | R4 | R5 | R6 | % YIELD* |
|---|---|---|---|---|---|---|---|
| 1A | H | OH | H | H | H | H | 45 |
| 1B | H | OH | H | H | NO2 | H | 85 |
| 1C | H | OH | H | H | Br | H | 45 |
| 1D | H | OH | H | OCH3 | H | OCH3 | 41 |
| 1E | H | OH | H | H | F | H | 40 |
| 1F | H | OH | H | F | H | H | 35 |
| 2A | H | OH | OCH3 | H | H | H | 8 |
| 2B | H | OH | OCH3 | H | NO2 | H | 28 |
| 2C | H | OH | OCH3 | H | Br | H | 20 |
| 2D | H | OH | OCH3 | OCH3 | H | OCH3 | 25 |
| 2F | H | OH | OCH3 | F | H | H | 16 |
| 3A | H | NO2 | OH | H | H | H | 12 |
| 3B | H | NO2 | OH | H | NO2 | H | 8 |
| 3C | H | NO2 | OH | H | Br | H | 7 |
| 3D | H | NO2 | OH | OCH3 | H | OCH3 | 7 |
| 3E | H | NO2 | OH | H | F | H | 10 |
| 3F | H | NO2 | OH | F | H | H | 14 |
| 4A | Cl | H | OH | H | H | H | 55 |
| 4B | Cl | H | OH | H | NO2 | H | 67 |
| 4C | Cl | H | OH | H | Br | H | 57 |
| 4D | Cl | H | OH | OCH3 | H | OCH3 | 46 |
| 4E | Cl | H | OH | H | F | H | 40 |
| 4F | Cl | H | OH | F | H | H | 62 |

6,156,723

COMPOSITIONS COMPRISING INHIBITORS OF ESTROGEN RESPONSE

This is a National Phase filing under 35 U.S.C. §371 of PCT Application PCT/US96/04104, filed on Mar. 26, 1996, which is a continuation in part of U.S. Ser. No. 08/410,807, filed Mar. 27, 1995, now U.S. Pat. No. 5,723,291, which is a continuation-in-part of U.S. Ser. No. 08/115,161, filed Sep. 1, 1993, now abandoned. The present application claims priority to and benefit of each of these applications, as provided for under 35 U.S.C. §119 and/or 35 U.S.C. §120, as appropriate. All of these applications are incorporated herein by reference in their entirety for all purposes.

BACKGROUND OF THE INVENTION

Many breast tumors require estrogens for tumor growth. Thus, treatment with antiestrogen compounds can slow or prevent tumor spread. Many antiestrogens, however, show both estrogen antagonistic and agonistic activity. The non-steroidal antiestrogen tamoxifen, for example, which is established as the treatment of choice for the endocrine therapy of advanced breast cancer, shows both agonistic and antagonistic activity. Sutherland, S. & Jackson, M. *Cancer Treat. Revs.* 15: 183–194 (1987).

The agonistic activity of tamoxifen and other antiestrogens may have profound effects upon patients. For example, agonistic activity may have beneficial effects, such as preventing osteoporosis and reducing serum cholesterol. Love, et al. *New Eng. J Med.* 326: 852–856 (1992). Love, et al. *J. Natl. Cancer Inst.* 82: 1327–1332 (1990). Conversely, agonistic activity may also be harmful. Tamoxifen for example sometimes increases endometrial tumor incidence lino, et al. *Cancer Treat. & Res.* 53: 228–237 (1991) or switches from inhibition to stimulation of estrogen dependent growth in breast tumor progression. Parker, M.G. (ed) Cancer Surveys 14: Growth Regulation by Nuclear Hormone Receptors. Cold Spring Harbor Laboratory Press (1992).

It is desirable to identify pure antiestrogens as they are anticipated to provide more rapid, complete or longer-lasting tumor responses. Wakeling, A. E. *Breast Cancer Res. & Treat.* 25: 1–9 (1993). For example, ICI 164,384 (hereinafter referred to as "ICI"), thought to be a pure antiestrogen, blocked MCF-7 cell invasion activity of a re-constituted basement membrane while estradiol and 4'-hydroxytamoxifen stimulated this activity suggesting that early treatment of breast cancer with a pure antiestrogen might be particularly beneficial in limiting tumor spread. Braacke, et al., *Br. j Cancer* 63: 867–872 (1991).

Conversely, while pure antiestrogens appear preferable for cancer treatments, mixed agonist-antagonist compounds may be preferable for preventative treatment. Such compounds should combine sufficient antagonist activity on estrogen stimulated breast tumor growth while maintaining simultaneous agonist activity on bone density and serum lipid levels.

In addition, a number of non-steroidal natural and synthetic compounds found in the environment have been shown to possess estrogenic activity. For instance, plant flavonoids including genistein and coumestrol and synthetic compounds such as phenolphthalein, alkylphenols, and dihydroxystilbenes, have been shown to be agonists of the estrogen receptor (Miksicek, *Mol. Pharmacol.* 44:37–43 (1993); Nieto et al., *Biochem. Int.* 21:305–311 (1990); White et al., *Endocrinology* 135:175–182 (1994); Makela et al., *Environ. Health Perspect.* 102:572–578 (1994); Krishnan et al. *Endocrinology* 132:2279–2286 (1993)).

Environmental estrogens, or xenoestrogens, are suspected of playing a role in the causation of a number of diseases such as breast and other cancers. In addition, such compounds may be implicated in human infertility and problems in wildlife reproduction. In the case of breast and other cancers, established risk factors (e.g., genetic factors) do not always account for the high levels of these diseases. Evidence suggests that lifetime exposure to various xenoestrogens may be important in the induction of breast cancer. To the extent such xenoestrogens are important in diseases such as breast cancer, reduction in exposure to these compounds should be critical to reducing cancer risks (Davis et al. *Environmental Health Perspectives* 101:372–377 (1993)).

Currently, antiestrogen compounds or xenoestrogenic compounds are screened with animal models such as the rat uterine test. These tests are cumbersome, slow, expensive and of uncertain application to humans because of differences between the human and rodent estrogen receptors.

The prior art fails to provide methods for quickly and easily testing potential antiestrogen compounds for agnostic as well as antagonistic properties mediated through pathways other than the classical estrogen response pathway, that may affect, adversely or beneficially, their use in various therapeutic applications. In addition, the ability to quickly and inexpensively screen environmental compounds for estrogenic activity is particularly important for assessing health consequences of new and existing chemicals. This invention addresses these and other problems in the art.

SUMMARY OF THE INVENTION

The present invention provides methods for screening test compounds, for example environmental compounds, for the ability to activate or inhibit transcription through an indirect estrogen response or classical estrogen response. The indirect estrogen response is mediated by promoters comprising an AP1 site and the classical estrogen response is mediated by promoters comprising a classical estrogen response element. Preferred AP1 sites can be isolated from metalloprotease genes. Preferred classical estrogen response elements can be isolated from the Xenopus vitellogenin A2 gene.

The methods typically use cells comprising an estrogen receptor and a promoter comprising an AP1 site which regulates expression of a reporter gene. The cells are then contacted with the test compound and the expression of the reporter gene is detected. The methods are conveniently used for testing compounds known to be antiestrogens for the ability to activate transcription through the AP1 site.

In other embodiments the assays are used to test environmental compounds for estrogenic activity. Environmental estrogens will typically be non-steroidal compounds, which are effective agonists of the estrogen receptor. Such compounds may be tested for their ability to activate transcription through the classical estrogen response element or through the AP1 site. For this purpose, cells which express mutant estrogen receptors are conveniently used. Cells expressing mutant estrogen receptors with lower activity are useful in decreasing background transcription. A preferred cell is the ERC1 cell line.

Cells derived from a source other than breast tissue are generally preferred for measuring activation mediated by the AP1 site. For example, uterine cells such as Ishikawa cells can be used. The reporter genes used to detect an estrogen response include genes encoding beta-galactosidase and bacterial chloramphenicol acetyl transferase. The promoters used may be those which naturally comprise AP1 or estrogen receptor elements or the promoters may be genetically engineered to comprise those elements.

In some embodiments a single cell may comprise two promoters, each with either the AP1 or the classical estrogen response element. In these embodiments, two different reporter genes are operably linked to the two promoters. In these assays the ability of test compound to induce or inhibit both the indirect and classical pathways can be determined.

When the methods are used to identify estrogen antagonists, the test compounds are contacted with the cells and a compound known to mediate an indirect estrogen response. The ability to inhibit the response is determined by detecting the expression of the reporter gene. Compounds known to mediate an indirect estrogen response include tamoxifen and estrogen at half maximal concentrations. The compounds can also be tested for the ability to induce or block the classical estrogen pathway, as well.

Estrogen antagonists identified using this assay include genistein, staurosporine, 6-thioguanine, and 2-aminopurine. These estrogen antagonists block the indirect estrogen response. Thus, in another embodiment, this invention provides a method of inhibiting agonistic activity of an antiestrogen compound. The method involves administering with the antiestrogen compound with one of the above-identified antagonists, or functionally equivalent analogues (e.g., inhibitors of mitogen activated protein (MAP) kinase phosphorylation of ER). In a particularly preferred embodiment, these antagonists are used in conjunction with tamoxifen. The inhibition can be in vivo or in vitro.

This invention also provides for an estrogen response inhibiting composition comprising a combination of an inhibitor of the classical estrogen response (classical pathway) and an inhibitor of an indirect estrogen response. The inhibitor of the indirect estrogen response can include any of the above-identified antagonists or functionally equivalent analogues. In a particularly preferred embodiment, the inhibitor of the classical estrogen response pathway is tamoxifen.

BRIEF DESCRIPTION OF THE DRAWINGS

FIG. 2A shows CAT assays of HeLa cells transfected with the indicated reporter genes and 3 μg of human ER expression vector. Representations, at left, show the human collagenase promoter (shaded) and the consensus AP-1 site. CAT activities were from cells maintained in the absence of hormone or saturating concentrations of ICI 164,384 (ICI, 1 μM), tamoxifen (5 μM) or estradiol (100 nM). CAT activity is normalized to a transfection control with the actin promoter driving expression of βHCG. Single representative experiments are shown, error bars represent standard deviation of triplicate hormone treatments. FIG. 2B shows CAT assays of HeLa cells transfected with reporter genes consisting of sequences overlapping the collagenase AP-1 site (−73 to −52) upstream of the herpes simplex virus TK promoter (from −109 to +45 relative to the start site of transcription) or the native TK promoter alone. FIG. 2C shows CAT assays of HeLa cells transfected with reporter genes containing classical EREs.

FIGS. 3A and 3B show that antiestrogen agonism at AP-1 sites requires ER. FIG. 3A shows dose dependence of estrogen and antiestrogen induction of col173-LUC in HeLa cells relative to input ER expression vector, normalized to constant input DNA with blank expression vector SG5. The luciferase assays were normalized to actin-HCG and were expressed relative to values that were obtained with the collagenase promoter in the absence of expression vector and hormone. A single representative experiment with triplicate points is shown. Error bars represent standard deviations. FIG. 3B shows concentration dependence of estrogen and antiestrogen induction of col173-LUC in HeLa cells. HeLa cells were transfected with 5 μg of ER expression vector and the collagenase promoter active upon a luciferase reporter gene. The cells were exposed to a range of concentrations of ligand. Error bars represent standard deviation of triplicate points.

FIG. 4A and 4B show that tarnoxifen is an agonist in endometrial Cells but not in breast cells. FIG. 4A shows the response of the transfected col173-CAT reporter in Ishikawa cells treated with estrogen or antiestrogen. Left panel, col173-CAT response with endogenous ER contrasted with the response of an ERE regulated reporter, ERE-col160CAT. Right panel, col173-LUC response with 3 μg co-transfected expression vector for human ER. Averages of three individual experiments are shown. FIG. 4B shows activity of the collagenase promoter in breast cell lines with endogenous ER. Left panel shows response of the collagenase promoter driving CAT in MCF7 cells (average of four experiments). Right panel shows activity of the coil promoter driving luciferase expression in ZR75 cells, either without or with 300 ng of human ER expression vector. A single representative experiment with triplicate hormone treatments is shown.

FIG. 5A shows potentiation of hormone responses in HeLa cells by Jun and Fos. Relative luciferase activities, normalized to HCG production, and calculated relative to collagenase expression in the absence of ER and hormones are presented. The errors represent standard deviations of three separate experiments. FIG. 5B shows effects of ER with and without transfected Jun and Fos on hormone induction of the collagenase promoter in F9 cells. Averages of five or six individual transfections are shown. FIG. 5C shows response of the collagenase promoter in F9 cells to increasing amounts of Jun, Fos, or their combination, in the absence of ER.

7B) with expression vector for the ER derivative whose structure is indicated. CAT or Luciferase activities, normalized to HCG production are shown. Activator plasmids, are shown schematically at the left of the figure. The VP16 transactivation domain is represented as an oval. The GAL4 DNA binding domain is marked.

Figure 8A:
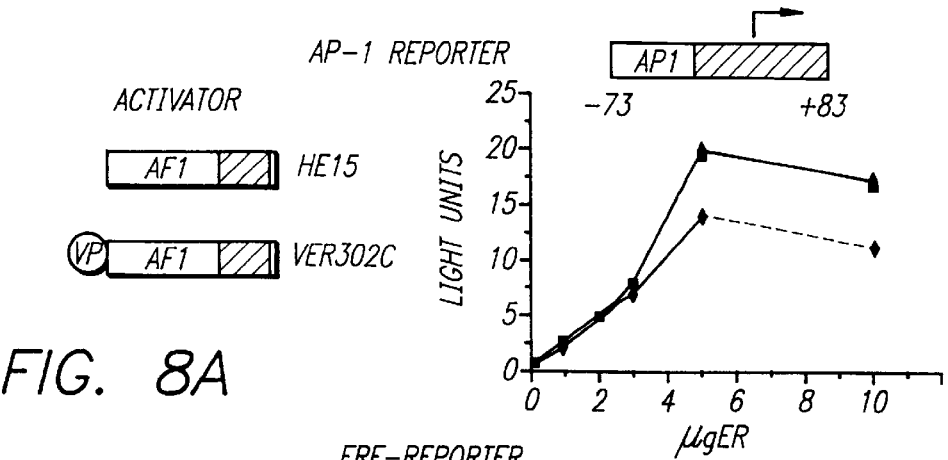
Figure 8B:
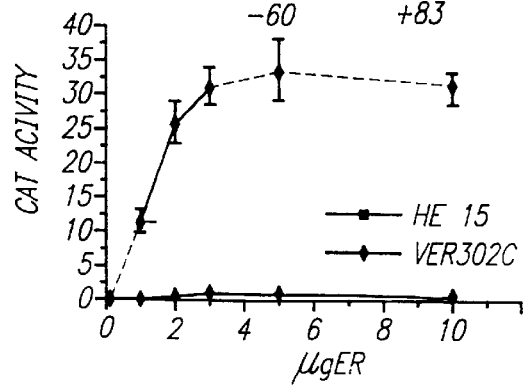

FIGS. 8A and 8B show that fusing an exogenous transactivation function to an ER derivative without the ligand binding domain potentiates gene expression mediated by an ERE but not by an AP-1 site. A luciferase reporter regulated by an AP-1 site (left panels) and a CAT reporter regulated by an ERE (right panels) were introduced into HeLa cells with expression vector for ER derivatives. CAT or Luciferase activities, normalized to HCG production, are shown.

Figure 9:
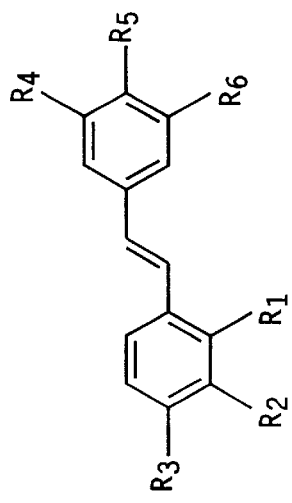

FIG. 9 shows a library of hydroxystilbene derivatives tested in the assays of the invention.

Figure 10:
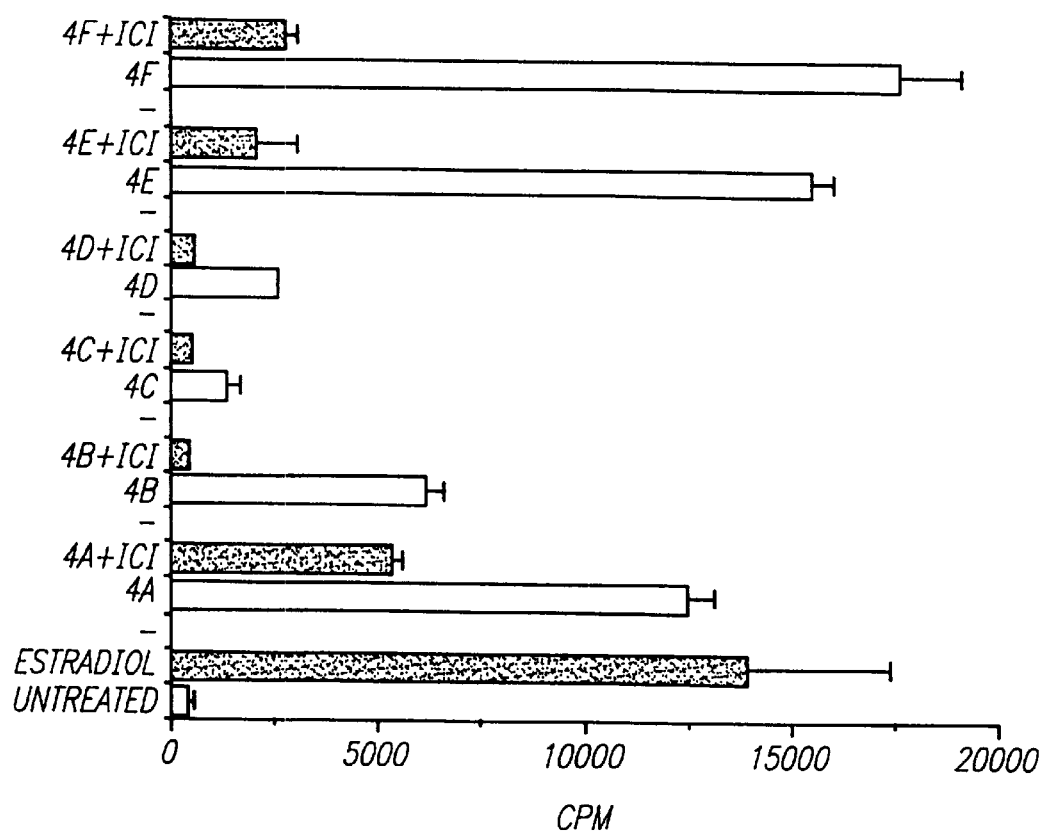

FIG. 10 shows estrogenic activity of series 4 compounds illustrated in FIG. 9 as well as inhibition of activity by treatment with ICI.

Figure 11:
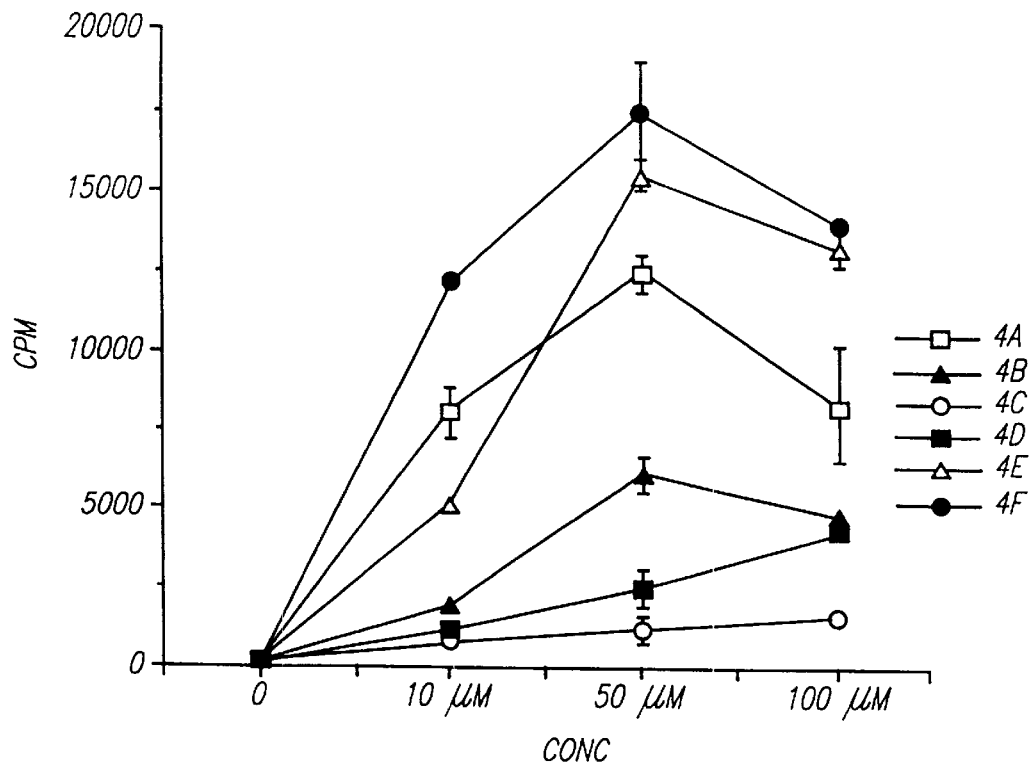

FIG. 11 shows dose response curves for series 4 compounds.

Figure 12:
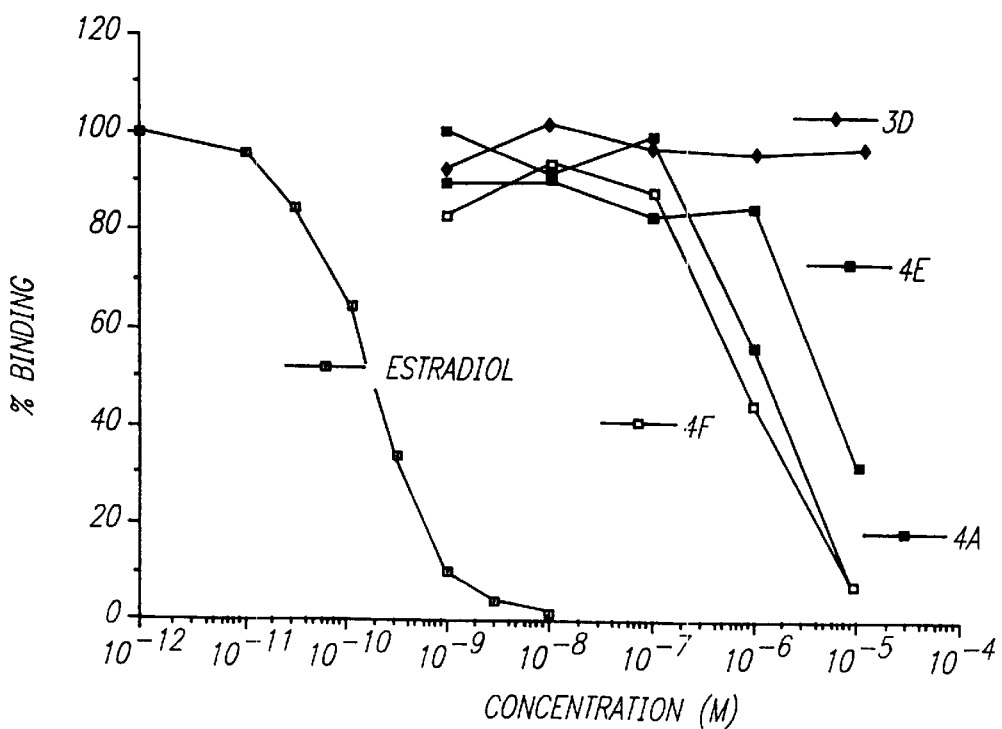

FIG. 12 shows results of ER binding/competition assays for series 4 compounds.

DESCRIPTION OF THE PREFERRED EMBODIMENT

The present invention provides an efficient way to screen large numbers of test compounds for those which have desirable properties for either the treatment or the prevention of various cancers (e.g., breast cancer, ovarian cancer, endometrial cancer) and other diseases (e.g., endometriosis) mediated by estrogen. The invention thus provides methods of screening for novel types of antiestrogen compounds that block the indirect estrogen response and/or block estrogen action at classical estrogen response elements. As used herein an antiestrogen is a compound that substantially inhibits estrogen activity as measured in a standard assay for estrogenic activity, for example, cellular assays as described in Webb et al. *Mol. Endocrinol.*, 6:157–167 (1993).

The invention also allows for screening of test compounds for estrogenic activity. The assays are particularly useful for screening environmental compounds suspected of having estrogenic activity, referred to here as xenoestrogens. Xenoestrogens are defined here to include any compound having estrogenic activity in the assays described herein, which is derived from a source outside the human body. Environmental compounds as used herein can be derived from a wide variety of sources including plants, soil, water, foods. They also include synthetic compounds such as chlorinated organics, polycyclic aromatic hydrocarbons, herbicides, pesticides, pharmaceuticals and the like.

In animals and in man the balance between stimulatory and inhibitory activities of antiestrogens such as tamoxifen varies widely depending on the organ, cell or specific protein measured as an indicator of estrogenic activity. This variety of effects is difficult to reconcile with the model of antagonism of estrogen receptor (ER) activity at classical estrogen receptor elements (EREs) as described in Beato, M. *Cell*, 56: 335–344 (1989) and Klein-Hitpass, et al., *Nucleic Acids Res.*, 16: 647–663 (1988).

The present invention relies, in part, on the discovery that ERs may activate transcription by interaction with another response element, the AP1 binding site, instead of binding to EREs. This AP1 mediated pathway, referred to here as the indirect estrogen response (in contrast to the classical estrogen response which is mediated through an ERE), may account for much of the agonistic properties of tamoxifen and other putative antiestrogens. A general description of the AP1 site is found in Angel & Kann, *Biochem. Biophys. Acta.*, 1072: 129–157 (1991) and Angel, et al., *Cell*, 49: 729–739 (1987).

In the methods of the invention, both the classical estrogen response elements and the indirect estrogen response may be used to provide a screening system that detects both estrogen antagonistic and agonistic activity. When testing an environmental compound for estrogenic activity, the methods typically comprise cultured cells that produce high levels of the human estrogen receptor. Such cells include MCF-7 cells (ATCC No. HTB 22), MDA453 cells (ATCC No. HTB 131), ZR-75-1 cells (ATCC No. CRL 1500) or ERC1 cells described in Kushner et al., *Mol. Endocrinol.*, 4:1465–1473 (1990). ERC2 and ERC3 cells as described by Webb, et al. *Mol. Endocrinol.*, 6:157–167 (1993).

Cells expressing mutant estrogen receptors with decreased sensitivity for estrogenic compounds are preferred for testing environmental compounds. Cells expressing the wild type receptor (e.g., MCF7 cells) have high background levels of transcription even in the absence of hormone. Transcription induced by weakly active environmental compounds may be masked in these cells. Thus, preferred cells for this purpose include cells which overexpress mutant estrogen receptors, such as the ERC cells noted above.

When testing an antiestrogen compound's ability to activate transcription through the AP1 mediated pathway, the source of the cells used in the assay can influence the results. In particular, evidence provided below indicates that agonistic activity of an antiestrogen (e.g., tamoxifen) is usually strong in cells in which its agonistic activity at an ERE is weak, and weak in cells in which its agonistic activity at an ERE is strong. As shown below, antiestrogens show little or no agonistic activity through the AP1 pathway in breast cancer cell lines. Thus, when testing antiestrogens for agonistic activity in the AP1 pathway, cells other than breast cancer cell lines are usually used. For instance, cells of uterine origin such as cervical cells (e.g., HeLa cells) or endometrial cells (e.g., Ishikawa cells) can be used. The invention is not limited to practice in mammalian cells and may be practiced, for example in yeast and insect cells, transfected with the appropriate genes and recombinant constructs.

The cells may be modified to provide truncated or chimeric estrogen receptors as described in Berry, et al., *EMBO J.*, 9: 2811–2818 (1990). These modifications may result in increased estrogen affinity and increased sensitivity of the assay.

In addition, these cells are transfected with reporter genes in which a response element (either the AP1 site or ERE) regulates expression of a reporter gene.

Typically, two different reporter genes are used. One gene reports transcription induced by the classical estrogen response system, while the other gene reports transcription induced by the indirect estrogen response. The two reporter genes and response elements are typically placed in separate cells, but the methods can also be used with both constructs in the same cell.

The reporter gene for the classical estrogen response system contains an estrogen response element (ERE) upstream of the target promoter and capable of regulating that promoter. In a preferred embodiment the ERE may be the consensus estrogen response element AGGTCACAGT-GACCT (SEQ ID NO: 1) from the Xenopus vitellogenin A2 gene.

The particular ERE used in the cells is not a critical aspect of the invention and the present invention is not limited to the use of this ERE. Other EREs known to one of skill in the art can also be used. For instance, other sources of naturally occurring EREs include the B2 gene, the chicken ovalbumin gene, and the PS2 gene. Alternatively, non-naturally occurring EREs may be inserted into particular promoters. The consensus ERE from the Xenopus vitellogenin A2 gene is widely used for this purpose, but other EREs may be used as well.

The reporter gene for the indirect estrogen response pathway contains an AP1 site upstream of the target promoter and capable of regulating that promoter. The AP1 site is a sites that are bound by AP1 (the Jun and Fos proteins) or other members of that protein family. In a preferred embodiment, the consensus AP1 site is TGA(C/G)TCA.

One of skill would recognize that the particular AP1 site used is not a critical aspect of the invention. Any sequence capable of being bound by AP1 or members of that family and regulating a promoter is suitable. This would include promoters which encompass a naturally occurring AP1 site. Typical promoters include, but are not restricted to metalloprotease genes such as stromelysin, gelatinase, matrilysin, and the human collagenase gene.

Alternatively promoters may be constructed which contain a non-naturally occurring AP1 or related binding site. This facilitates the creation of reporter gene systems that are not typically found under the control of AP1. In addition, promoters may be constructed which contain multiple copies of the AP1 site thereby increasing the sensitivity or possibly modulating the response the reporter gene system.

The present invention is not limited to a particular reporter gene. Any gene that expresses an easily assayable product will provide a suitable indicator for the present assay. Suitable reporter genes are well known to those of skill in the art. They include, for example, bacterial chloramphenicol acetyl transferase (CAT), beta-galactosidase, or luciferase.

One of skill will recognize that various recombinant constructs comprising the AP1 site can be used in combination with any cell or line which expresses, or contains an estrogen receptor. An estrogen receptor, as used herein, includes an estrogen receptor in its native (naturally occurring) form as well as modified estrogen receptors. Numerous modifications of estrogen receptors are known to those of skill in the art. These include, but are not limited to V-ER, a chimeric receptor comprising the strong VP16 transcriptional activation domain linked to the amino terminus of the ER, V-ER in which the ER DNA binding domain (DBD) is deleted, H11 an ER lacking the DNA binding domain, and the like (see e.g., Kumar et al., *Cell*, 51: 941–951 (1987)).

To screen a number of compounds for antiestrogen action, cells with high level expression of human estrogen receptors and harboring either or both response elements and reporter genes are exposed to doses of estrogen which give half maximal induction or less. In each case this will result in induction of several to hundreds of fold depending on the levels of estrogen receptor and the particular details of the reporter construction. This will be reflected in increases of the reporter gene product, such as the CAT gene product which may be quantitated by enzymatic assay. The cells can be exposed to estrogens either growing in separate wells of a multi-well culture dish or for colorometric assay in a semi-solid nutrient matrix. The antiestrogenic compounds to be tested are added to the culture dish wells or to small wells made in the semi-solid matrix and the effect on the estrogen induction is assayed. An antiestrogen compound will reduce or abolish the estrogen induced increase in reporter gene activity. A hypothetical pure antiestrogen will block estrogen action with both types of reporter genes and will have no ability to induce the reporter genes in the absence of estrogen. A mixed estrogen antagonist-agonist, will show some ability to induce the reporter genes, especially the reporter genes linked to AP1 site.

In other embodiments, environmental compounds suspected of having estrogenic activity are contacted with cells with high level expression of human estrogen receptors and harboring either or both response elements and reporter genes as described above. Those compounds with estrogenic activity will result in induction of several to hundreds of fold depending on the levels of estrogen receptor and the particular details of the reporter construction. Quantification of the activity by enzymatic assay can be carried as described above.

An assay for detection of xenoestrogens can be conveniently provided in kit format. Such a kit includes growth media, estrogen standards, and cells comprising the appropriate recombinant constructs. The kits may also include reagents suitable for detecting the product of the reporter gene, and the like.

Antiestrogens which block the indirect pathway (e.g., genistein, staurosporine, 6-thioguanine, 2-aminopurine, or analogues that show the same mode of activity (i. e, are functionally equivalent) on the indirect response pathway) can be used to supplement tamoxifen or other antiestrogens in the treatment or prevention of breast cancer and other diseases mediated by estrogen. These compounds function to eliminate estrogenic agonistic activity of antiestrogens. Second they may have uses by themselves. In particular, it may be advantageous to block some estrogen mediated pathological effects at indirect estrogen response elements while leaving the direct pathway active. Compounds that block the indirect pathway are useful as components of combined oral contraceptives (COC) containing estrogens and progestins. A triple COC, containing estrogens, progestins, and a blocking compound would allow estrogen, either in the formulation or endogenous to act at the classical response elements, but would block action at the indirect response elements. Thus, a triple COC functions as current COCs to prevent pregnancy, but may also provide protective effects against breast cancer.

Typically, the reporter gene linked to the AP1 site is activated, not with estrogen, but with an excess (10 times the Kd) of tamoxifen, 4-hydroxy tamoxifen, or other antiestrogen. A library of compounds is searched for candidates that block or reduce reporter gene activation by the antiestrogen. The candidates are then tested with cells containing the reporter gene for the classical pathway to confirm that they do not interfere with estrogen activation at an ERE.

Antiestrogen or estrogen compounds identified in the assays of the invention can be used in standard pharmaceutical compositions for the treatment of cancer, as components of oral contraceptives, or any other application in which the modulation of estrogen activity is desired. The pharmaceutical compositions can be prepared and administered using methods well known in the art. The pharmaceutical compositions are generally intended for parenteral, topical, oral or local administration for prophylactic and/or therapeutic treatment. The pharmaceutical compositions can be administered in a variety of unit dosage forms depending upon the method of administration. For example, unit dosage forms suitable for oral administration include powder, tablets, pills, and capsules.

Suitable pharmaceutical formulations for use in the present invention are found in *Remington's Pharmaceutical Sciences*, Mack Publishing Company, Philadelphia, Pa, 17th ed. (1985). A variety of pharmaceutical compositions comprising compounds of the present invention and pharmaceutically effective carriers can be prepared.

The following examples are offered by way of illustration, not by way of limitation.

EXAMPLE 1

MATERIALS AND METHODS

Plasmid Construction

All reporter genes described below have been modified by digestion with EcoRl and Ndel to remove an AP-1 site in the backbone of pUC. Thus, Col173 and Col160 are formerly ΔCol173 and ΔCol160 (Lopez et al. *Mol. Cell. Biol.* 13:3042–930 (1993)). Col173-LUC was constructed by cloning a BamHI/PvuII fragment, that spanned the luciferase transcription unit, from pMG3 into col173, which had been digested with BamHI and SmaI to remove the CAT transcription unit. EREcol160 and EREcol173 was prepared by ligation of a consensus ERE (AGGTCACAGTGACCT), (SEQ ID NO: 1) into the HindIII site upstream of col160 and col173, respectively. All other reporter genes have been previously described (Webb et al. *MoL Endocrinol.* 6:157–16725 (1992); and Lopez et al., supra).

Expression vectors for ER and ER mutants (Kumar et al. *Cell* 51:941–51 (1987)), VP16-ER (Elliston et al. *J Biol Chem* 265:11517–21 (1990)), c-jun (Tumer et al. *Science* 243:1689–94 (1989)) and c-fos (Sassone et al. *Cell* 54:553–60 (1988)) have been described. For this study, all ER cDNAs were cloned into the EcoRI site of the SG5 expression vector (Green et aL *Nucleic Acids Res* 16:369 (1988)).

The VP16ER cDNA was also cloned into SG5, to form the vector VER, in two steps. The expression vector Vp16ER1-422 (Elliston et al., supra) was digested with SstI, repaired with T4 polymerase, and ligated to EcoRI linkers. The resulting EcoRI fragment was sub-cloned at the equivalent site of SG5 to generate the vector VER1-422. This was digested to completion with HindIII and BglII and the equivalent (HindIII/BamHI) fragment from HEO was replaced at this location. VERΔDBD was constructed by substituting a NotI/BglII fragment from HE11 (cloned in SG5) into VER digested with the same enzymes.

The GST wild type ER fusion gene (GST-HEGO) was constructed by ligation of the EcoRI fragment from pSG5-HEGO, spanning the ER cDNA, into pGEX5X-1, one of the vectors of the pGEX series (Pharmacia Biotech Inc., Piscataway, N.J., USA). GST-hELBD was constructed in two steps. An Xba fragment from HE19G was inserted into the equivalent position of XbaI digested SG5-HE14, which spans the ER LBD (Kumar et al.). Then, an EcoRI fragment spanning this ER cDNA was cloned into pGEX-3X. To prepare GST-hEN 185 an EcoRI/KpnI fragment spanning the ER amino terminus was obtained from the vector EGE, repaired and cloned into pGEX-5X-1 digested with SmaI and EcoRI.

Tissue Culture and Transfections

Cells were maintained and transfected as previously described in Webb et al., supra. Hormones were added two hours after plating in the following concentrations, estradiol 100 nM, ICI 164,384 1 μM, tamoxifen 5 μM, to ensure saturation of the response. F9 cells were seeded at 30% confluence upon 1.5 cm dishes and transfected overnight by calcium phosphate coprecipitation with 5 μg reporter gene, 1 μg actin β-HCG, and 1 μg of HEO, 300 ng each of c-jun and c-fos expression vectors. The cells were glycerol shocked and refed in growth medium containing hormone or ethanolic vehicle. In transient transfections, optimal amounts of HEO were employed and were as follows: HeLa (5 μg); NIH3T3 (1 μg); HepG2 (1 μg); SHM (300 ng); SY5Y (300 ng); CEF (100 ng); CV-1 (3 μg); MDA453 (3 μg); CHO (100 ng) and F9 (1 μg).

CAT assays were carried out as described in Webb et al., except that the cells were harvested one to two days after transfection instead of three. CAT activities were defined as the increase in cpm per hour at room temperature (corrected for background) per 100 μl of cell extract, normalized to production of 100 standard units of βHCG, from a co-transfected reporter gene, actin-HCG. Luciferase assays were performed as described by Brasier et al. Methods Enzymol 216:386–97 (1992)) on similar extracts that were used for CAT assays. Light units were defined as the luciferase activity per 100 μl of cell extract per 100 standard units of βHCG. Relative luciferase activities were calculated with respect to the results that were obtained in the absence of ER and hormone, which was set at 1 unit. For the data presented in Table I triplicate points were determined. Standard deviations were less than 20%.

GST Fusion Protein Binding Assay and in vitro Translation

Procedures were carried out as described by Lopez et al., supra. Briefly, fusions of GST to various domains of the human ER were prepared as follows. Bacteria expressing the fusion proteins were resuspended in buffer IPAB-80 (20 mM REPES, 80 mM KCl, 6 mM $MgCl_2$, 10% Glycerol, 1 mM DTT, 1 mM ATP, 0.2 mM PMSF and protease inhibitors; pH 7.9), sonicated mildly, and the debris was pelleted at 12,000 rpm for I hr in an ss34 rotor. The supernatant was incubated for 2 hrs. with 500 μL of glutathione sepharose 4B beads that were previously washed with 5 volumes of PBS 0.2% Triton X-100 and equilibrated with 5 volumes of IPAB 80. GST-fusion proteins beads were then washed with 5 volumes of PBS 0.05% Nonidet P-40 and resuspended in 1 ml of IPAB-80 for storage at 4 C. until use. All the above procedures were done in a cold room at 4° C.

Assays of GST-ER fusions were carried out in 100 μL volume that contained 40 μL of bead suspension (equivalent to 10 μL of compact beads volume) and 1 to 2 μL of 35S in vitro translated c-jun or c-fos in IPAB-80 2.5% non fat milk and incubated for 1.5 hr at 4° C. Beads were washed 5 to 6 times with IPAB-80 containing 0.05% Nonidet P-40. Input labeled proteins, proteins bound to GST, GST-hER and other ER fusion beads were then subjected to SDS polyacrylamide gel electrophoresis (PAGE) in 10% acrylamide and then to autoradiography.

RESULTS

Antiestrogens Activate Transcription Through the AP1 Site.

The human collagenase gene, like other matrix metalloproteases, responds to AP1. The promoter from this gene contains a consensus AP-1 site located between –60 and –73 base pairs from the start of transcription. Angel, et al., *Mol. Cell. BioL.*, 7: 2256–2266 (1987). To test whether an AP1 site could confer estrogen response the collagenase promoter was fused to the bacterial CAT gene (Δcol173) and transfected into Chinese Hamster Ovary cells that overexpress ER (ERC1) (Kushner, et al. *Mol. Endocrinol.* 4: 1465–1473 (1990)).

Figure 1A:
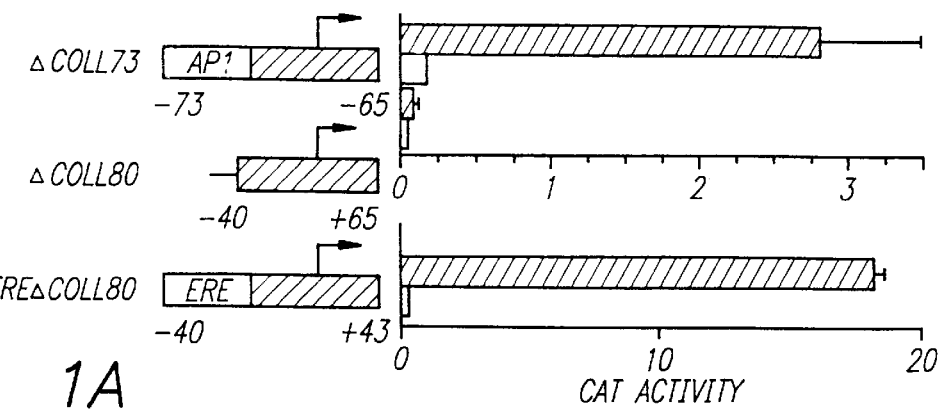
FIGS. 1A and 1B show estrogen stimulation mediated by an AP1 site in ERC1 cells (FIG. 1A) and F9 cells (FIG. 1B). Typical results of CAT assays, normalized for transfection efficiency, following a single transfection are shown opposite. Each point is the mean value of triplicate assays, with standard errors. CAT activities from cells maintained in the absence of hormone are shown as white bars, those in the presence of a saturating concentration (100 nM) of estradiol as black bars.

Estradiol stimulated Δcol173 ten fold (FIG. 1A), whereas a similar reporter in which the AP1 site had been removed (Δcol160), gave reduced basal activity and no estrogen response. Substitution of a classical ERE (Klein-Hitpass, et al., *Nucl. Acids Res.* 16: 647–663 (1988)) for the AP1 site (EREΔcol160), restored estrogen response, but not the elevated basal activity.

Figure 1B:
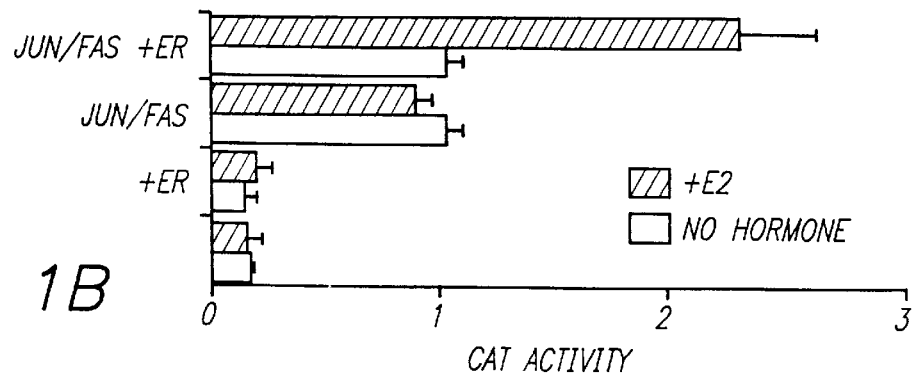

In F9 cells, which lack endogenous AP1 activity (Chiu, et al. *Cell*, 54: 541–551 (1988)) Δcol173 failed to respond to estrogen in the presence of transiently transfected ER (FIG. 1B). Estrogen activation could be restored by cotransfecting expression vectors for AP1 proteins c-Jun and c-fos. Sassone-Corsi, P. et al., *Cell*, 54: 553–560 (1988). Turner & Tjian, *Science* 243: 1689–1694 (1989). In parallel, EREΔcol160 was estrogen responsive, even in the absence of AP1, and Δcol160 and remained unaffected by estrogen (data not shown). Estrogen induction of the collagenase promoter therefore required both the AP1 site and AP1 proteins.

Figure 2A:
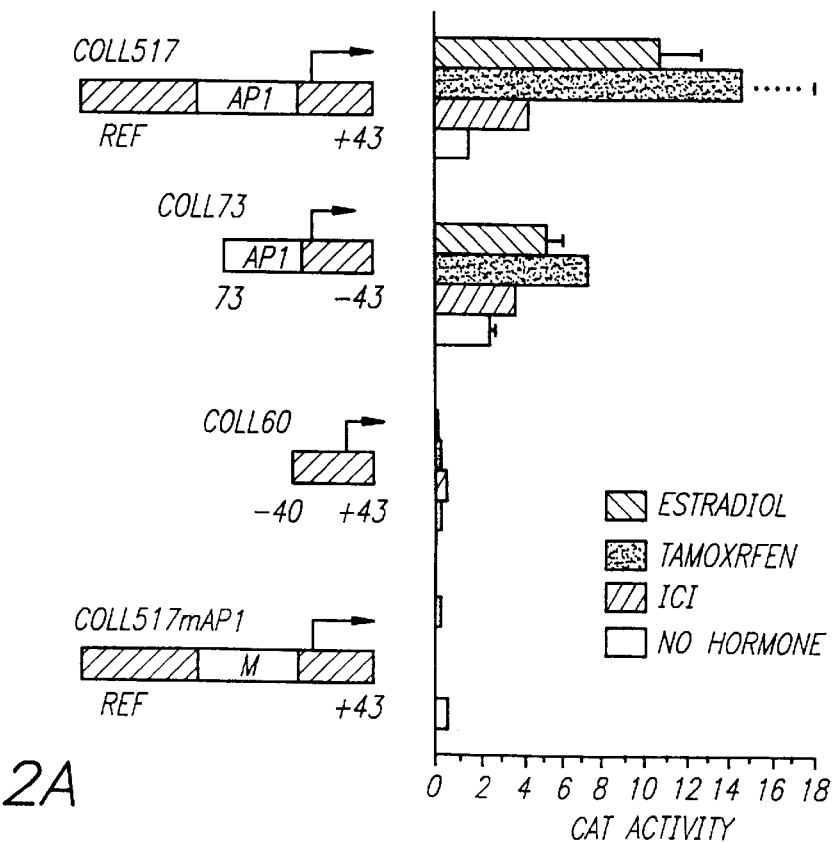
FIGS. 2A–2C show antiestrogen stimulation of expression in an intact AP-1 Site, but not at classical EREs.
Figure 2B:
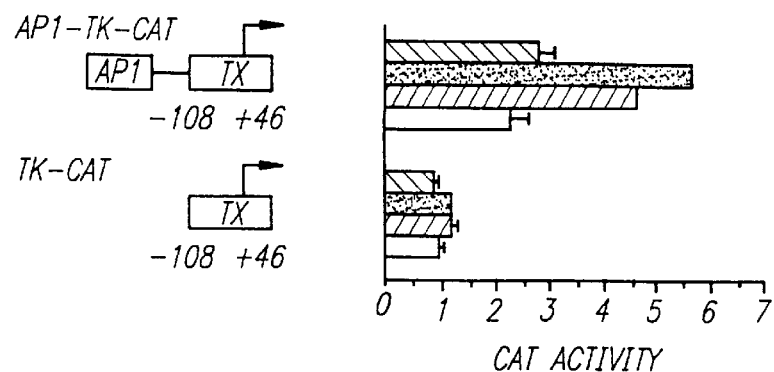

To further examine the effects of antiestrogens on the AP-1 directed pathway, reporter genes derived from the human collagenase promoter were transfected into HeLa cells. Both estrogen and antiestrogens activated the collagenase promoter in the presence of transiently expressed human ER (col1517, FIG. 2A). In these cells tamoxifen was more potent an activator than estrogen. This pattern was retained with col173, but was lost with col160 or was inactivated by point mutations (col1517mAP1).

When the collagenase AP-1 site was placed upstream of the herpes virus tk promoter both tamoxifen and ICI were able to activate transcription, although this response was not as robust as with the native collagenase promoter (FIG. 1B). These results indicate that antiestrogens are agonists at the collagenase promoter and a heterologous promoter linked to AP-1. Thus, the AP-1 site is required for this activity.

Figure 2C:
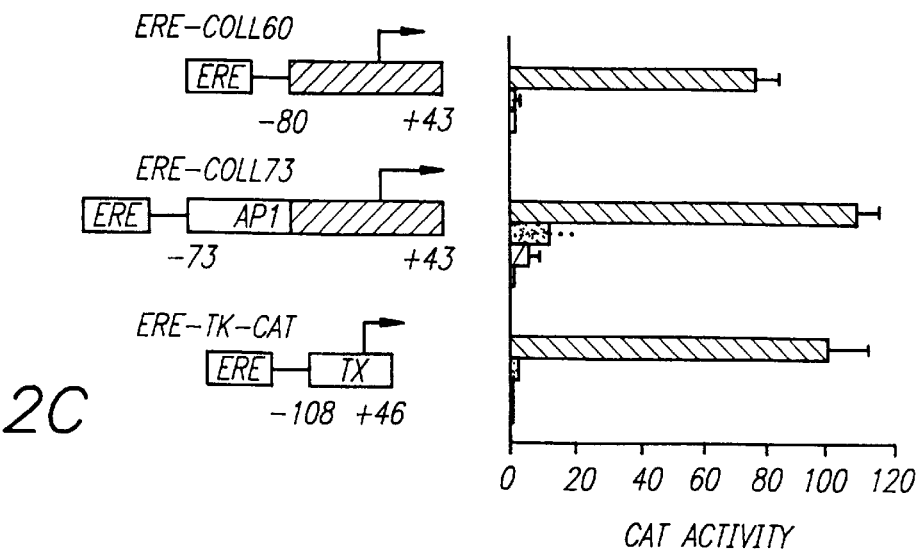

The activity of antiestrogens in the AP-1 pathway was also compared with their activity in the classical pathway. Direct substitution of an ERE for the collagenase AP-1 site restored estrogen response to the core collagenase promoter, but not antiestrogen response or the basal activity associated with the AP-1 site. A promoter with both an ERE and an AP-1 site (ERE-col173 FIG. 2C) gave a large estrogen response, but retained some response to antiestrogens. Another control reporter, in which the tk promoter was regulated by a classical ERE (ERE-tk FIG. 2C) was also activated by estrogen, but not by antiestrogens. Thus, a classical ERE cannot substitute for the AP-1 site, indicating that the AP-1 site has a unique function in activation by antiestrogens.

Figure 3A:
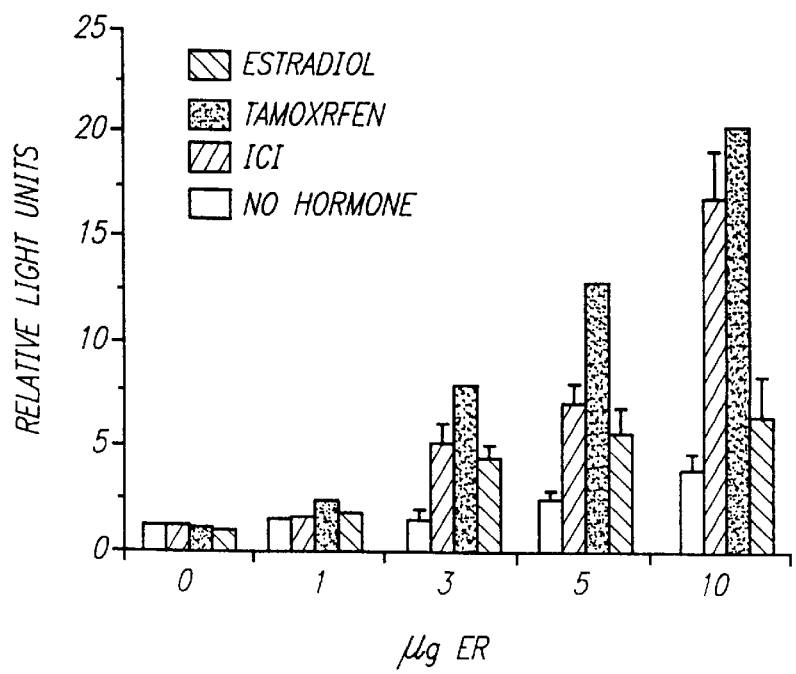

To determine whether ER was required for antiestrogen agonism the response of the collagenase promoter, upstream of the luciferase gene (col173-LUC), to transfection of increasing amounts of ER into HeLa cells was examined (FIG. 3A). Estrogen and antiestrogen responses were not seen in the absence of ER, and increased as a function of the amount of transfected ER expression vector. Tamoxifen responses were more potent than estrogen responses at every level of receptor.

The effect of increasing doses of each ligand was also examined. FIG. 3B shows that the half maximal dose for ICI is about 10 times, and tamoxifen 100 times, that for estrogen. This is consistent with the known binding affinities of these compounds to the estrogen binding site on the receptor and suggests that they are stimulating transcription through that site. Similar half maximal doses were obtained for both estrogen and the weak tamoxifen responses that were seen at a classical ERE (data not shown).

In summary, indirect estrogen response is widely active, and antiestrogens are agonists of this pathway. it is possible that any of the well described agonist effects of tamoxifen reflects indirect estrogen response. Antiestrogens would have estrogenic activity on critical AP1 regulated target genes, hence growth and differentiated response, in cells in which ER and AP1 proteins could interact. Changes in AP1 during tumor progression could be particularly significant, and should be considered in models of antiestrogen resistance in breast cancer. Parker, et al. *Cancer Surveys*, 14, Growth Regulation by Nuclear Hormone Receptors. Cold Spring Harbor Laboratory Press (1992).

Antiestrogens Are Agonists of the AP-1 Pathway in Many Cell Types

The data above show that antiestrogens are agonists at the AP-1 driven collagenase promoter, but not at classical EREs, in HeLa and other cells. To test whether this pattern was widespread, the effect of estrogen and antiestrogens on the expression of reporter genes driven by either the native collagenase promoter, or a similar promoter in which the AP-1 site was replaced by a classical ERE, was tested in a range of cell lines. In each case, the cells were transfected with different amounts of the human ER expression vector HEO to determine the optimal response.

Table I shows that both estrogen and antiestrogens activated the collagenase promoter in most cell types. This response occurred with cell lines representative of different tissue types including cervix, liver, myometrium, neuroblastoma, kidney and ovary. In most cases tamoxifen was as potent, or more potent, than estrogen. Only F9 cells, which have low levels of endogenous AP-1 activity, were not activated by any ligand.

In the same range of cell types both antiestrogens displayed little activity at classical EREs (data not shown). ICI consistently behaved as a pure antagonist of ER action at an ERE. In HeLa cells, and most other cases, tamoxifen inductions of ERE-col160 activity remained at less than 3% of those obtained with estrogen. Significant (30% of estrogen) tamoxifen inductions at classical EREs were obtained in CEF cells and CV-1 cells and MDA453 cells. In these latter cells tamoxifen action at the AP-1 site was relatively weak (Table I). Thus, tamoxifen activity at an AP-1 site may be strong in cells at which its activity at an ERE is weak (HeLa), and weak at an AP-1 site in cells at which its activity at an ERE is strong (MDA453).

In conclusion, antiestrogen agonist effects occur at AP-1 sites in cells of diverse origin. These effects show little correlation with the activity of tamnoxifen at classical EREs.

Antiestrogens are Agonists of the AP-1 Pathway In Endometrial Cell Lines, But Not in Breast Cells The data in Table I show that, in most cell types, tamoxifen was at least as potent as estrogen in inducing the collagenase promoter. In one cell line, MDA453 breast cancer cells, the AP-1 driven collagenase promoter was activated efficiently by estrogen but not by tamoxifen. Similarly, in Chinese hamster ovary (CHO) cells, estrogen inductions routinely exceeded antiestrogen inductions. This suggests that tamoxifen action at the collagenase promoter might have a cell specific component.

To further explore this phenomenon, and to test whether similar hormone effects could be detected at physiological levels of ER, the expression of the collagenase promoter in cells that express endogenous ER was examined. Ishikawa cells, an endometrial cell line that is believed to represent a model of tamoxifen agonism on the uterus (described by Holinka, et al., *J. Steroid Biochem.*, 25: 781–786 (1986)), and two breast cancer cell lines, MCF-7 and ZR-75-1, both of which are known to respond to estrogen but not tamoxifen, were used.

In Ishikawa cells (FIG. 4A) the collagenase promoter was activated by estrogen and tamnoxifen, but the ICI compound was usually inactive in the presence of endogenous receptor. This parallels the reported potency of tamoxifen and ICI on cell growth and induction of progesterone receptors in these cells. When receptor levels were raised by transfection, tamoxifen and estrogen inductions became larger and ICI inductions became detectable. In contrast, neither ICI nor tamoxifen activated expression of ERE-col160, whereas estrogen induced expression of this reporter gene tenfold. Tamoxifen also failed to activate several other genes that contain simple classical EREs in Ishikawa cells (data not shown).

In MCF-7 cells, estrogen, but not tamoxifen, activated the collagenase promoter (FIG. 4B). The same pattern occurred in ZR-75-1, and could be seen more clearly when extra receptors were supplied by transfection. Again, this resembles the results that were obtained in MDA453 cells (Table I), and parallels the reported absence of tamoxifen effects on cell proliferation and gene expression in breast cancer cell lines.

In conclusion, tamoxifen activates the collagenase promoter in cells with physiological levels of ER, and the response shows tissue restrictions. Tamoxifen activity occurs in endometrial cells, but not in breast cells, and thus parallels the known tissue specificity of tamoxifen agonism.

TABLE I

| Cell Line | Origin | Col73 Luciferase Activity (*1) | | | |
|---|---|---|---|---|---|
| | | No Hormone | ICI | Tam | E2 |
| HELA | CERVIX | 1.0 | 3.7 | 7.4 | 3.4 |
| NIH 3T3 | FIBROBLAST | 1.0 | 3.0 | 3.1 | 3.3 |
| HEP G2 | LIVER | 1.0 | 5.2 | 6.5 | 4.3 |
| SHM | MYOMETRIUM | 1.0 | 1.9 | 2.2 | 2.0 |
| SY5Y | NEUROBLASTOMA | 1.0 | 2.3 | 2.1 | 2.1 |
| CEF | FIBROBLAST | 1.0 | 3.2 | 2.2 | 2.5 |
| CV-1 | KIDNEY | 1.0 | 3.1 | 5.3 | 2.2 |
| MDA453 | BREAST | 1.0 | 1.1 | 2.1 | 8.4 |
| CHO | OVARY | 1.0 | 1.8 | 2.2 | 3.3 |
| F9 (*2) | TERATOCARCINOMA | 3.2 | 2.4 | 1.1 | 1.4 |

*1. Activities were determined in triplicate transfections. Activities were normalized to an actin-HCG internal control and expressed relative to values obtained from the collagenase promoter in cells that were not transfected with ER or treated with hormone (see Materials and Methods). Standard deviations (not shown) were less than 20%.
*2. Unliganded ER increased the basal activity of the collagenase promotor.

AP-1 Proteins Are Required for ER Action at the Collagenase Promoter

Figure 5A:
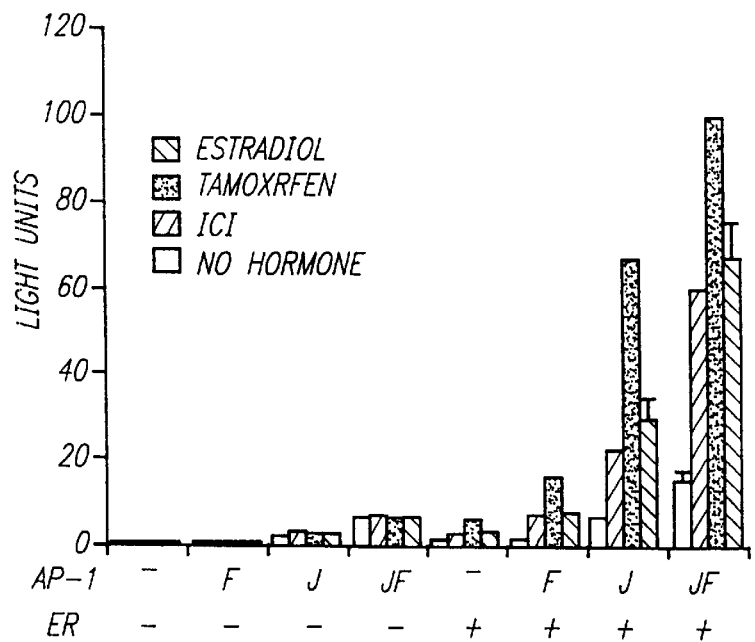
FIGS. 5A–C show that hormone response at the AP-1 site requires AP-1 proteins.

To test whether AP-1 proteins, as well as their cognate binding site, were required for the AP-1 pathway, we examined whether Jun and Fos overexpression affected the hormone response of the collagenase promoter. The Examples above establish that antiestrogens and estrogens activate the collagenase promoter in HeLa cells in the presence of ER (see, e.g., Table I). FIG. 5A shows that these inductions are markedly increased by the presence of transfected AP-1, especially in the presence of Jun or Jun/Fos. This suggests that Jun homodimers or Jun/Fos heterodimers occupying the AP-1 site contribute to the ability of ER to activate description in the AP-1 directed pathway.

To confirm that AP-1 proteins were absolutely required for the AP-1 directed ER pathway, we turned to F9 cells, which have only low levels of endogenous AP-1 activity. Transfection of an expression vector for estrogen receptor into these cells did not support hormone activation of the collagenase promoter (Table I), whereas it gave strong estrogen activation at an ERE (not shown). Co-transfection of ER with Jun/Fos restored induction by both estrogen and antiestrogens in F9 cells, albeit at lower levels than that seen in HeLa cells. In addition there was some activation by unliganded ER. Thus, the inability of F9 cells to allow a hormone response at the collagenase promoter can be overcome with AP-1 supplied by transfection. We conclude that hormone effects at the AP-1 site require AP-1 protein. However, the dramatic difference between the hormone response of HeLa and F9 cells when both are supplied with Jun and Fos indicates that other cell specific factors, in addition to AP-1 abundance, regulate the strength of the AP-1 directed ER pathway.

Figure 5B:
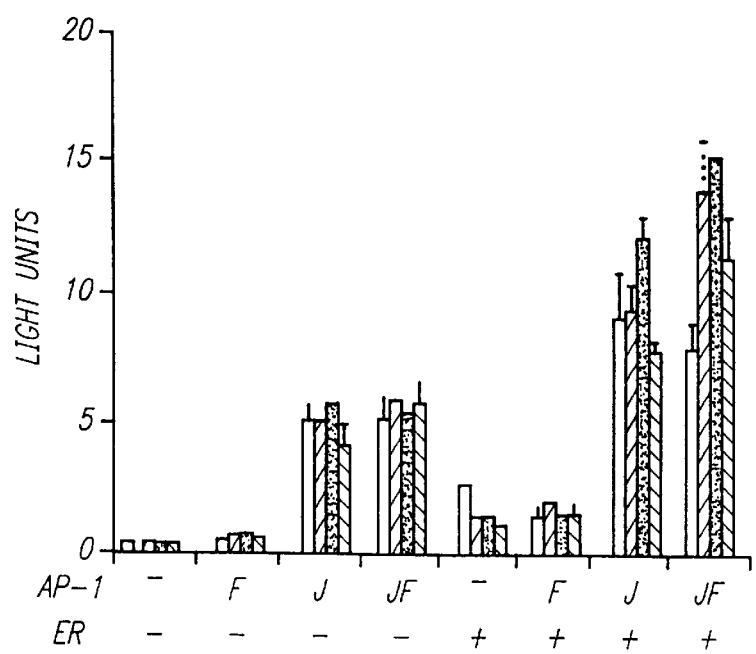
Figure 5C:
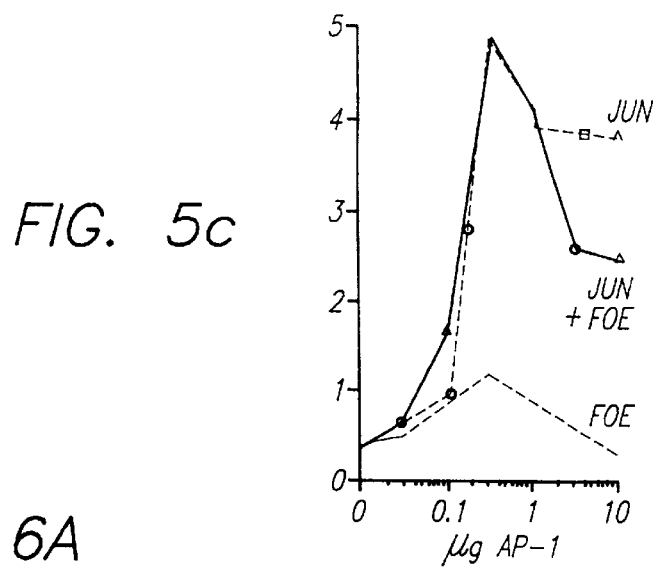

It is unlikely that ER dependent activation at AP-1 sites is due to changes in the amount of AP-1. In these studies we determined the amounts of AP-1 required for optimal collagenase promoter activity in F9 cells. FIG. 5C shows that Jun, Fos, and a combination of both, increased basal activity of the collagenase promoter (in the absence of ER) which reached a maximum with 300 ng of expression vector. These amounts were employed in the co-transfections with ER (FIG. 5B). Thus, ER activation at AP-1 sites appears to increase the transcriptional efficiency of Jun and Fos even when they are provided at optimal amounts.

ER Binds Jun But Not Fos in vitro

To test whether ER effects upon AP-1 might reflect direct biochemical interaction between the ER and AP-1 proteins, we examined whether they specifically interact in solution. An estrogen receptor protein fused to glutathione S-transferase (ER-GST), and attached to agarose beads, pelleted in vitro translated Jun from solution, whereas a control GST protein pelleted only background amounts of Jun. Similar binding occurred with the ER amino terminal domain, but not with the LBD. Neither the intact ER nor its isolated domains bound Fos. These results indicate that Jun, but not Fos, binds ER in vitro, and that a major target of Jun is the ER amino terminus.

Tamoxifen Activation at AP-1 Requires the ER DBD, Whereas Estrogen Activation Is DBD Independent In Some Cell Types.

Figure 6A:
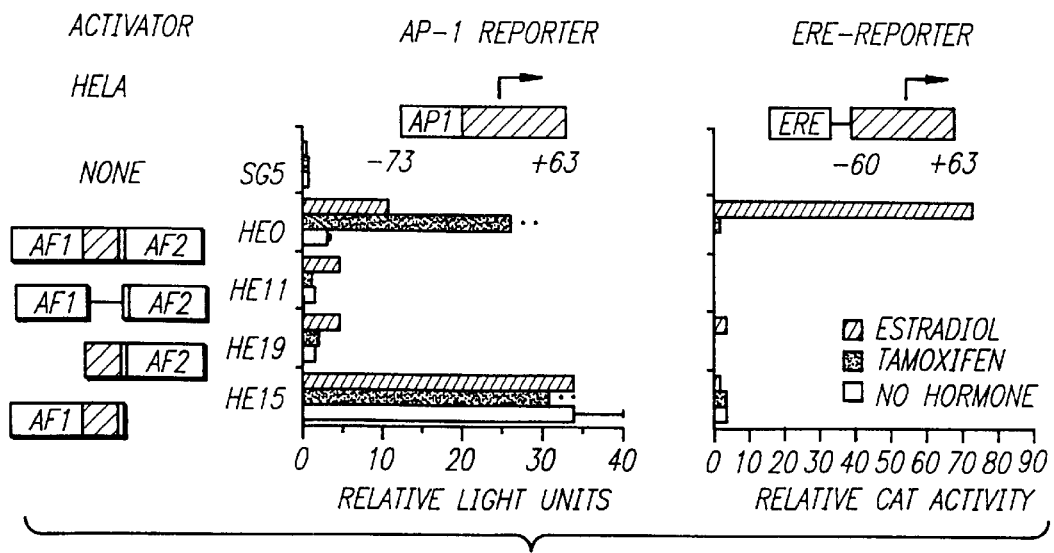
FIGS. 6A–C show that the DNA binding domain of ER is required for tamoxifen induction at an AP-1 site, but not required for estrogen induction. Reporters regulated by an AP-1 site (left panels), or an ERE (right panels) were introduced into HeLa (FIG. 6A), CHO (FIG. 6B), or MDA453 cells (FIG. 6C), with 5 μg, 100 ng and 1 μg respectively of each expression vector for the ER derivative whose structure is indicated. The DNA binding domain is indicated with the striped box, the ligand binding domain (AP2) and the amino terminal (AF1) activation functions are marked. Results are presented for col173-LUC in HeLa and MDA453 cells and col173-CAT in CHO cells. CAT and luciferase activities are calculated relative to those obtained with col173-LUC or col173-CAT with SG5 blank expression vector in the absence of hormones.

We next examined which domains of the ER mediate hormone action. We introduced truricated derivatives of the ER into three different cell types. We chose the HeLa, CHO and MDA453 lines as recipients because the ER driven AP-1 pathway showed different properties in each cell. In HeLa cells tamoxifen response predominated, in MDA453 cells estrogen response predominated, and CHO cells gave an intermediate phenotype (Table I). We examined the ability of each truncated ER to activate a reporter gene driven by the collagenase promoter with its AP-1 site (FIG. 6, left side) or a reporter gene driven by control promoter with an ERE (FIG. 6, right side). Previous work has established that each of these variant ERs is expressed at comparable levels from these vectors.

Deletion of the DNA binding domain (DBD) completely eliminated estrogen activation at an ERE in all three cell types (HE11, FIG. 6). Deletion of the DNA binding domain also eliminated tamoxifen activation at AP-1 sites, be it the substantial tamoxifen activation in HeLa and CHO cells, or the marginal amount in MDA cells. In contrast, removal of the DBD did not abolish estrogen activation at the AP-1 site in any of the cell lines. Indeed, estrogen activation at the AP-1 site in CHO cells was equally strong with or without the ER DBD. This is consistent with previous observations that estrogen response at AP-1 sites shows independence of DNA binding in CEF. Thus, the requirement for the ER DBD varies according to the ligand, it is required for tamoxifen induction but not estrogen induction. We suggest below (Discussion) that the differential requirements for the ER DBD may indicate the existence of more than one pathway of ER action at AP-1 sites.

The ER amino terminus also played an important role in tamoxifen and estrogen activation at the AP-1 site. Although deleting of the amino terminus (HE19) did not eliminate activity upon the ERE regulated reporter in all three cell types, this deletion abolished the strong tamoxifen-activation at the AP-1 site in HeLa cells and the weaker tamoxifen activation in CHO and MDA453 cells. Deletion of the amino terminus also markedly reduced estrogen activation at the AP-1 site in all three cell types.

A deletion of the ligand binding domain (HE15), leaving the amino terminus and DBD intact, gave a constitutively active receptor that was able to weakly activate at an ERE in all three cell lines. This receptor, however, showed highly potent activity at the AP-1 site in HeLa cells, which correlated with the levels of activity obtained with the tamoxifen liganded native ER. In contrast, HE15 was inactive in MDA453 cells and weak in CHO cells. Thus, the requirement of the ER amino terminus for AP-1 activation also shows cell type specificity, in a manner that correlates with the cells ability to support a tamoxifen response at the collagenase promoter. This again suggests that activation through AP-1 may occur through more than one mechanism.

ER Can Target an Exogenous Transactivation Domain to the Collagenase Promoter, Independently of the ER DBD One possible mechanism for ER activation at AP-1 sites is that the receptor might directly bind to the AP-1 complex at the promoter and from there influence transcription. A prediction of this model is that ER should be able to target heterologous transcriptional activation functions to an AP-1 regulated promoter.

Figure 7A:
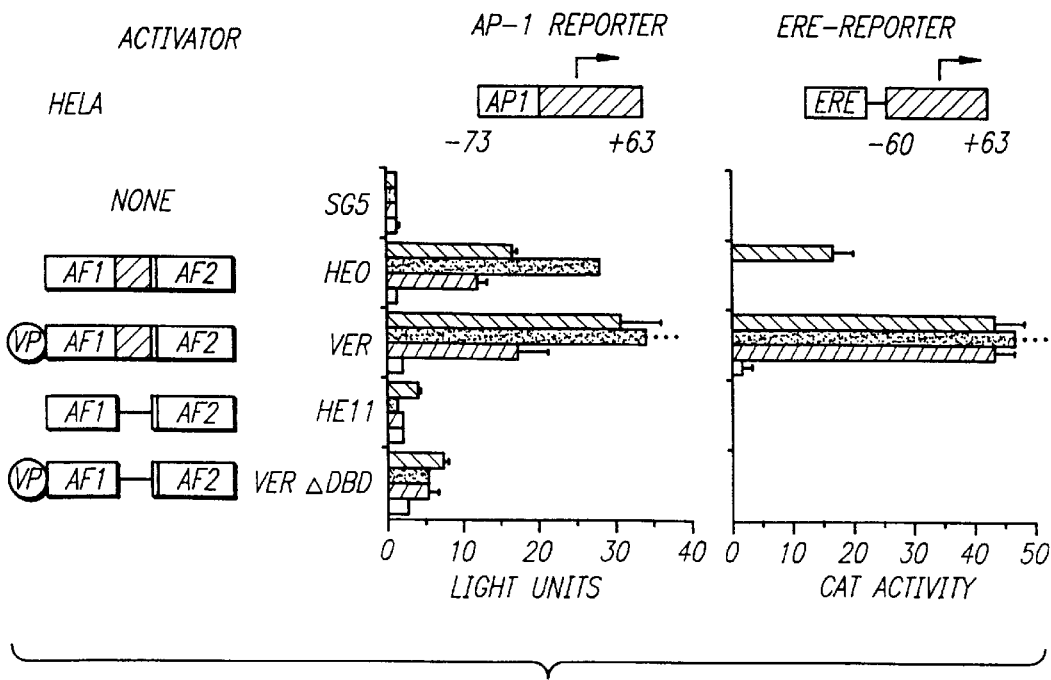
FIGS. 7A and 7B show that fusing an exogenous transactivation function to the ER increases activation at AP-1 sites. A luciferase reporter regulated by an AP-1 site (left panels) and a CAT reporter regulated by an ERE (right panels) were introduced into HeLa (FIG. 7A), CHO (FIG.

In order to test this proposition, we examined the effects of linking the strong VP16 transcriptional activation domain to the amino terminus of the ER (V-ER). To monitor activity we used a luciferase reporter gene regulated by an AP-1 site and CAT reporter gene driven by an otherwise identical promoter with an ERE. The V-ER chimeric receptor gave markedly enhanced activation at an ERE in HeLa cells (FIG. 7A). It was activated both by estrogen and antiestrogens reflecting the ability of VP16 to override the need for AF-2 (see, Kumar et al Cell 51:941–951 (1987)), and consistent with previous reports for this "super-receptor". In contrast, the super-receptor had little effect at the AP-1 site in HeLa. Tamoxifen activation with the full length ER was hardly increased, although estrogen activation was modestly potentiated. We also tested a version of the super-receptor in which the ER DBD was deleted (VERΔDBD). This receptor, as expected, failed to activate at an ERE. It was, however, more potent than an equivalent ER (HE 11) that lacked the VP16 activation function when tested at an AP-1 site.

Figure 6B:
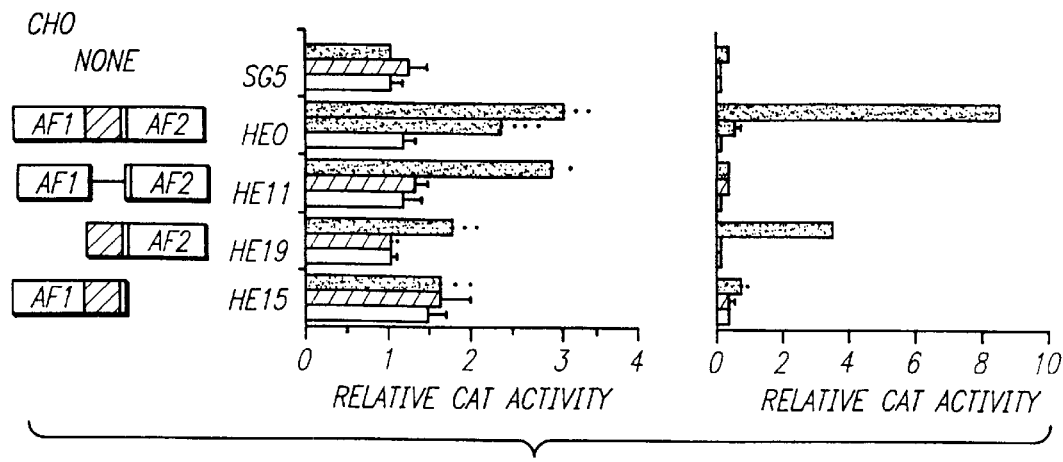
Figure 6C:
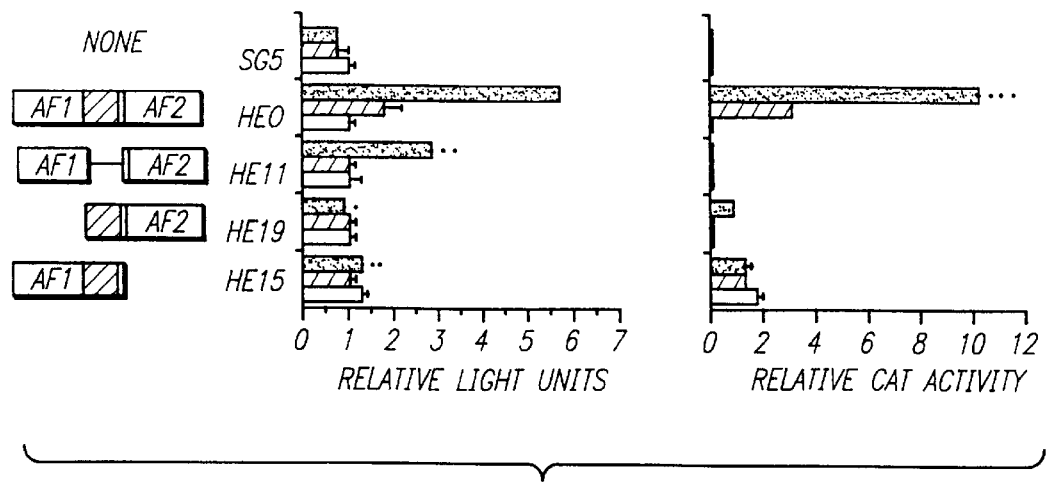
Figure 7B:
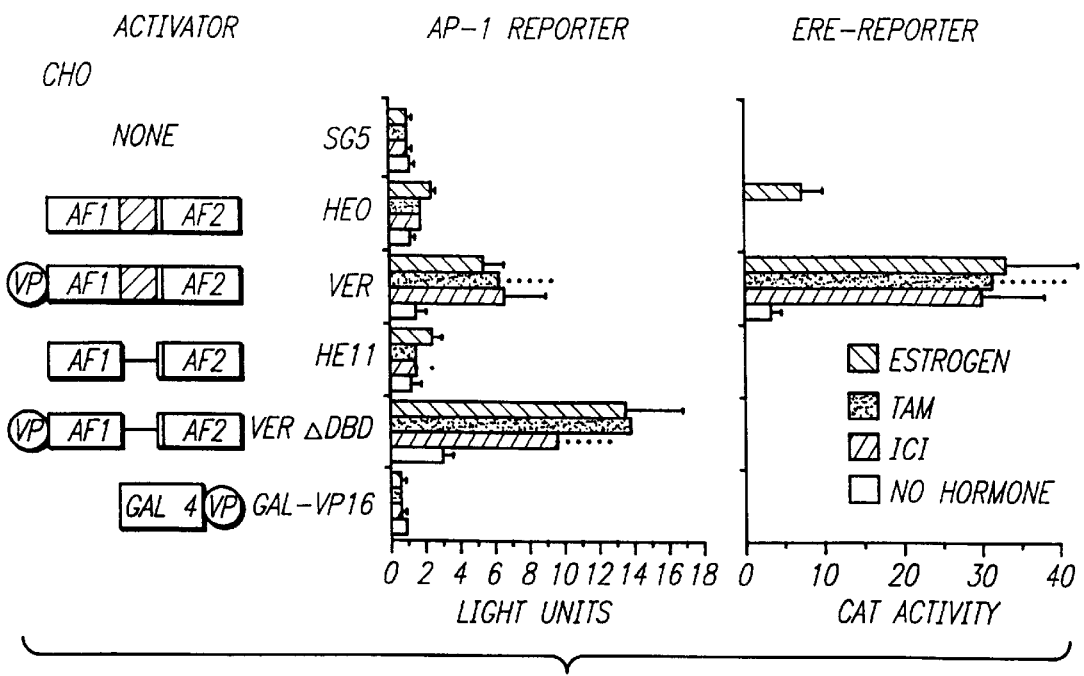

To further explore this phenomenon we performed a series of similar experiments in CHO cells (FIG. 7B), in which estrogen response at the AP-1 site was completely independent of the ER DBD (FIG. 6B). Once again, the V-ER chimera superactivated gene expression that was driven by the ERE. In this case, however, V-ER also superactivated at the AP-1 site. Although the superreceptor that lacked the DBD (VERΔDBD) remained unable to activate transcription from an ERE, it was even more active than V-ER at the AP-1 site. A control fusion of the VP16 domain to the yeast GAL4 DNA binding domain did not increase collagenase promoter transcription. Thus, the superactivation by VP 16 in CHO cells is dependent upon sequences in the ER protein. These observations indicate that super-receptors are super-activators at AP-1 sites in CHO cells in a DBD-independent manner. Similar results were also obtained with MDA453 cells (data not shown). The contrast between the properties of the super-ER in HeLa and CHO cells further suggests that there may be more than one pathway of activation at AP-1 sites.

VP16 Potentiates the Action of an ER Without an LBD at an ERE, But Not at an AP-1 Site.

The results described above suggest that addition of the VP 16 activation function to native ER was unable to strongly potentiate tamoxifen action at an AP-1 site in HeLa cells. We also observed that an ER lacking the LBD (HE15) was a potent constitutive activator of the AP-1 pathway in HeLa, and that this correlated with the ability of these cells to support a large tamoxifen response at the collagenase promoter. To directly test whether transcriptional activation functions were involved in this pathway, we examined the effects of fusing the VP16 activation domain to this receptor (V-ER302C, FIG. 8). FIG. 8B shows that the presence of the VP16 domain greatly potentiated transcription from an ERE, but failed entirely to potentiate transcription activation by ER from the AP-1 site (FIG. 8A). Indeed, the presence of the VP16 domain slightly decreased the activity of HE15 at the AP-1 site. Similar results were also obtained in CHO cells (data not shown). Thus the activation pathway of the LBD deleted receptor at AP-1 sites appears not to respond to exogenous transcriptional activation functions, We argue below that this suggests the existence of an ER pathway that activates transcription from AP-1 sites independent of ER associated transcriptional activation functions.

EXAMPLE 2

Estrogenic Activity Screens

A library of hydroxystilbene derivatives as shown in FIG. 9 was screened for estrogenic activity in cell culture assays using a CAT reporter gene linked to a classical ERE in ERC1 cells as described in Webb et al., supra. After transient transfection with CAT reporter genes, each hydroxystilbene was added to the cultured ERC 1 cells. ER-regulated response was compared either to treatment with 17β-estradiol as a calibration standard or to treatment with an ethanolic vehicle. Hydroxystilbene series 1, 2 and 3 showed no measurable estrogenic activity data (data not shown), whereas series 4 compounds showed weak estrogenic activity (FIG. 10). Of the series 4 compounds 4A, 4E and 4F were found to provide the highest levels of estrogenic activity relative to 170β-estradiol.

To examine whether the series 4 compounds induce estrogenic activity through the ER, we tested the ability of ICI 164384 to inhibit the series 4 estrogenic activity. The ICI 164384 compound was found to inhibit the estrogenic activity of all the series 4 compounds (FIG. 3). As a negative control, CHO cells, which lack functioning ER, were transfected with the same estrogen-responsive reporter constructs and treated with 170β-estradiol and the series 4 hydroxystilbenes. As expected, no estrogenic activity was seen with these cells.

Dose Response and ER Binding of Series 4

Dose response experiments were performed on the series 4 compounds over a concentration range of 0–100 $\mu$M (FIG. 11). For the most active compounds, 4A, 4E, and 4F saturation is observed at 50 $\mu$M. The effective concentration that provides 50% maximum activity ($EC_{50}$) ranges from −5 $\mu$M to ~15 $\mu$M for these three compounds. In vitro ER binding assays were performed on the three most active series 4 compounds to confirm that the estrogenic activity measured in the bioassay correlated with binding affinity for the ER. The inactive hydroxystilbene analog 3D was included in the binding assay as a negative control. The ER-binding results for compounds 4A, 4E and 4F are consistent with the estrogenic bioassay, as each of the compounds show $IC_{50}$ values of 1–10 μM for ER binding (FIG. 12). The two most active compounds in the bioassay, 4A and 4F, also show the highest affinity (1 μM) for the ER, although this affinity is approximately four orders of magnitude lower than that of 17βestradiol. The analog 3D which showed no activity in the bioassay also shows no binding affinity for the ER.

Additional experiments were performed to characterize further the estrogenic activity of the series 4 compounds identified in the initial screen. Four of the compounds (4A, 4B, 4E and 4F) showed clear dose response profiles over a concentration range of 0–100 μM (FIG. 10). The three most active compounds, 4A, 4E and 4F, show maximum activity at 50 μM and have $EC_{50}$ values for estrogen response in the range of 5–15 μM. Three lines of evidence suggest that the series 4 estrogenic response is mediated by direct binding of the hydroxystilbene to the estrogen binding site of the ER. First, the fact that no estrogenic activity was observed in reporter gene-transfected CHO cells which lack a functional ER provides evidence that the response to the series 4 compounds was ER-mediated. Second, the observation that the response initiated by all the series 4 compounds could be inhibited by ICI 164384, a potent steroidal antiestrogen that competes with 17β-estradiol for binding to the ER, provides evidence that the hydroxystilbenes act through direct binding to the steroid binding site on the ER. Third, the binding affinity of the series 4 compounds to the ER was directly measured in a competition binding assay with 17β-estradiol and the measured $IC_{50}$ values for the series 4 hydroxystilbenes correlate approximately with the $EC_{50}$ values measured from the dose response bioassay.

Structure-activity relationships (SAR) in both the hydroxy-substituted and distal aromatic rings of the hydroxystilbenes are evident from the varying estrogenic activities of the library. Based on the observation that activity was only seen in the series 4 compounds, it appears that a para orientation between the hydroxyl substituent and the stilbene olefin is a requirement for ER-binding and activation. The para orientation is sensitive to additional substitution as evidenced by the fact that no estrogenic activity was observed for the series 3 (4-hydroxy-3-nitro) compounds; it is unclear whether steric or electronic factors are responsible for the lack of activity in series 3. For the series 4 compounds, the three most active hydroxystilbenes bear either small fluorine substituents (4E, 4F) or no substitution (4A) in the distal aromatic ring. This distal ring SAR is somewhat subtle: based on the dose-response data, the 4'-Br substituted compound (4C) shows almost no activity, whereas the 4'-F substituted compound (4F) is the second most active member of the series. Here again, it is unclear whether steric effects, electronic effects, or a combination of both are responsible for the variations in estrogenic activity.

Conclusion

The above results show that three of the hydroxystilbene analogs permeate cell membranes and trigger a dose-dependent estrogenic response with $EC_{50}$ values in the range of 5–15 μM. Results from competition-response and ER-binding experiments with the antiestrogen ICI 164384 and 17β-estradiol provide evidence that the non-steroidal hydroxystilbene analogs elicit the estrogenic response through direct interaction with the steroid binding site of the estrogen receptor. In addition, structure-activity relationships for the hydroxystilbene pharmacophore are evident from the activity profile of the library. Such information could prove useful for predicting potential estrogenic activity of environmental pollutants and pharmaceuticals.

EXAMPLE 3

Identification of Inhibitors That Block Agonistic Effects of Antiestrogens

An estrogen receptor (ER) was transiently transfected into either HeLa or HepG2 cells along with an AP-1 responsive reporter gene, Col173-LUC. The transformed cells were then contacted with antiestrogens or estrogen in combination with prospective inhibitor drugs. In addition, a shortened constitutive version of the ER (HE15) that activates AP-1 activity in a cell specific manner which parallels the hormone dependent activity of native ER was also used. Luciferase was measured in cell extracts as an indication of AP-1 dependent promoter activity.

These assays identified several compounds that inhibit hormone action at AP-1 sites, but not the action of hormones at classical estrogen response element. This suggests that these compounds do not block estrogen receptor action per se, but rather interfere with the specific pathway that leads from the ER to AP1. The compounds also inhibit HE15 induction of AP-1 activity. The compounds include genistein, staurosporine, 6-thioguanine, and 2-aminopurine. These compounds are believed to inhibit mitogen activated protein (MAP) kinase phosphorylation of ER. Other compounds capable of inhibiting this activity are therefore also useful in inhibiting activation of AP-1.

More specifically, stauorsporine inhibited ER activation of the collagenase promoter in HepG2 cells. In this case, activation of AP-1 depends upon hormone because the native ER, which requires hormone for activity, is supplied.

Staurosporine, genistein, 6-thioguanine and 2 arninopurine inhibit the activation of AP-1 activity by HE15 in HeLa cells, whereas inhibitors of C-kinase (calphostin c), A-kinase (H89) and pl3-kinase (wortmannin) did not.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. An estrogen response inhibiting composition comprising:

an inhibitor of an indirect estrogen response selected from the group consisting of genistein, staurosporine, 6-thioguanine, and 2-aminopurine; and an inhibitor of a classical estrogen response pathway.

2. The composition of claim 1, wherein said inhibitor of a classical estrogen response pathway is tamoxifen.

3. The composition of claim 1, wherein said an inhibitor of an indirect estrogen response is genistein.

4. The composition of claim 1, wherein said inhibitor of an indirect estrogen response is staurosporine.

5. The composition of claim 1, wherein said inhibitor of an indirect estrogen response is 6-thioguanine.

6. The composition of claim 1, wherein said inhibitor of an indirect estrogen response is 2-aminopurine.

* * * * *